US012685982B2

(12) United States Patent
Liu et al.

(10) Patent No.: US 12,685,982 B2
(45) Date of Patent: Jul. 21, 2026

(54) GAS-LIQUID BUBBLING BED REACTOR, REACTION SYSTEM, AND PROCESS FOR SYNTHESIZING CARBONATE ESTER

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Yinchuan Liu, Shanghai (CN); Weisheng Yang, Shanghai (CN); Na Li, Shanghai (CN); Dizong Sun, Shanghai (CN); Wenjun He, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 1123 days.

(21) Appl. No.: 17/771,119

(22) PCT Filed: Oct. 23, 2020

(86) PCT No.: PCT/CN2020/123128
§ 371 (c)(1),
(2) Date: Apr. 22, 2022

(87) PCT Pub. No.: WO2021/078239
PCT Pub. Date: Apr. 29, 2021

(65) Prior Publication Data
US 2022/0410104 A1    Dec. 29, 2022

(30) Foreign Application Priority Data

Oct. 25, 2019    (CN) ......................... 201911025449.2

(51) Int. Cl.
B01J 8/08 (2006.01)
B01J 8/02 (2006.01)
(Continued)

(52) U.S. Cl.
CPC ............. B01J 8/085 (2013.01); B01J 8/0278 (2013.01); B01J 8/10 (2013.01); C07D 317/36 (2013.01);
(Continued)

(58) Field of Classification Search
CPC ... B01J 8/085; B01J 8/0278; B01J 8/10; B01J 2208/00867; B01J 2208/00884;
(Continued)

(56) References Cited

U.S. PATENT DOCUMENTS

| | | | |
|---|---|---|---|
| 3,963,446 A | 6/1976 | Miller | |
| 6,407,279 B1 | 6/2002 | Buchanan et al. | |
| 2016/0168112 A1* | 6/2016 | Naniki | B01J 31/0239 549/230 |

FOREIGN PATENT DOCUMENTS

| | | |
|---|---|---|
| CN | 101785981 A | 7/2010 |
| CN | 101838257 A | 9/2010 |

(Continued)

OTHER PUBLICATIONS

CN-106478583 A (Year: 2025).*

(Continued)

*Primary Examiner* — Huy Tram Nguyen
(74) *Attorney, Agent, or Firm* — FINNEGAN, HENDERSON, FARABOW, GARRETT & DUNNER LLP

(57) ABSTRACT

The present invention discloses a gas-liquid bubbling bed reactor, comprising a liquid distributor, a gas distributor (Continued)

located below the liquid distributor, a catalyst bed layer and a catalyst support plate, and an optional interception screen, wherein the top of the reactor is provided with a gas outlet, the reactor is provided with a feed inlet connected to the liquid distributor, a gas inlet connected to the gas distributor, the bottom is provided with a discharge outlet. The present invention further provides a reaction system, which comprises the gas-liquid bubbling bed reactor as the main reactor and a sub-reactor. Through the system and the process of the present invention, the problems of the low conversion rate, the gas binding of the circulating pump, the unstable operation, the low yield of electronic-grade products, and the like in the carbonate synthesis process are solved purposedly targetedly, and the present invention can be applied to related industrial production.

22 Claims, 1 Drawing Sheet

(51) Int. Cl.

| | | |
|---|---|---|
| *B01J 8/10* | (2006.01) | |
| *C07D 317/36* | (2006.01) | |
| *C07D 317/38* | (2006.01) | |

(52) U.S. Cl.

CPC ... *C07D 317/38* (2013.01); *B01J 2208/00867* (2013.01); *B01J 2208/00884* (2013.01); *B01J 2208/00938* (2013.01)

(58) Field of Classification Search

CPC .... B01J 2208/00938; B01J 2208/00876; B01J 8/082; B01J 2208/00176; B01J 2208/00283; B01J 2208/00911; B01J 8/08; B01J 8/22; B01J 8/087; C07D 317/36; C07D 317/38; C07C 68/04; C07C 69/96; Y02P 20/141

USPC ........................................................ 422/139

See application file for complete search history.

(56) References Cited

FOREIGN PATENT DOCUMENTS

| | | | | | |
|---|---|---|---|---|---|
| CN | 202379772 | U | | 8/2012 | |
| CN | 102675276 | A | | 9/2012 | |
| CN | 104801239 | A | * | 7/2015 | |
| CN | 106478583 | A | | 3/2017 | |
| CN | 106478586 | A | | 3/2017 | |
| CN | 106588862 | A | | 4/2017 | |
| CN | 106977402 | A | | 7/2017 | |
| CN | 108484565 | A | | 9/2018 | |
| CN | 110627764 | B | * | 8/2020 | .......... C07D 317/38 |
| ES | 2296949 | T3 | | 5/2008 | |
| GB | 2086256 | A | | 5/1982 | |
| GB | 0228119 | | | 1/2003 | |
| JP | S474758 | U | | 9/1972 | |
| JP | S501122330 | A | | 9/1975 | |
| JP | 2003183272 | A | | 7/2003 | |
| JP | 2006249066 | A | | 9/2006 | |
| JP | 2013075292 | A | | 4/2013 | |
| WO | WO 2004056794 | A1 | | 7/2004 | |
| WO | 2015008853 | A1 | | 1/2015 | |

OTHER PUBLICATIONS

CN-110627764 B (Year: 2025).*

Liaohe Petroleum Exploration of Liver Petroleum Exploration, *Liaohe Petroleum Exploration Petrochemical Records (1999-2009)*, Weblog Publishing Co., pp. 63-65, Dec. 31, 2011.

Extended European Search Report in counterpart European application No. 20878458.7, dated Jun. 6, 2023.

International Search Report and Written Opinion of International Application No. PCT/CN2020/123128, mailed Jan. 20, 2021.

* cited by examiner

GAS-LIQUID BUBBLING BED REACTOR, REACTION SYSTEM, AND PROCESS FOR SYNTHESIZING CARBONATE ESTER

CROSS-REFERENCE TO RELATED APPLICATIONS

This application is a national stage filing under 35 U.S.C. § 371 of International Application No. PCT/CN2020/123128, filed Oct. 23, 2020, which claims the priority to and benefits of Chinese Patent Application No. 201911025449.2, filed Oct. 25, 2019, which is incorporated herein by reference in its entirety.

TECHNICAL FIELD

The present invention relates to a gas-liquid bubbling bed reactor, more particularly a gas-liquid bubbling bed reactor for synthesizing carbonate; a reaction system; a process for synthesizing carbonate using the reaction system, more particularly a process for synthesizing carbonate by using alkylene oxide and carbon dioxide.

BACKGROUND TECHNOLOGY

Carbonate is a compound in which part or all of the hydrogen atoms of the two hydroxyl groups (—OH) in the carbonic acid molecule are substituted by alkyl groups. In the presence of strong acids, it will decompose into carbon dioxide and alcohol. Carbonate can be used in many aspects. Dimethyl carbonate can be used as a methylating agent. Dimethyl pyrocarbonate can be used as a preservative. Polycarbonate can be used as a polymer material. Ethylene carbonate and propylene carbonate can be used as polar solvents.

Taking carbonate as an example, in the prior art, there are mainly three synthesis methods, namely the phosgene method, transesterification method, and addition method of alkylene oxide and carbon dioxide.

The phosgene method refers to a method of preparing carbonate by reacting alcohol or phenol with phosgene. This is a commonly used method for preparing carbonate in the past, but because phosgene is highly toxic and causes serious pollution to the environment, this method has been banned in developed countries, so this method is gradually being replaced by other less polluting methods.

The transesterification method refers to a method of preparing carbonate by transesterification of dialkyl carbonate and alkane diol. The key to this method is to find a suitable catalyst.

However, the raw materials of this method are relatively expensive, and the efficiency of the catalyst is relatively low.

The addition method of alkylene oxide and carbon dioxide refers to a reaction of alkylene oxide and carbon dioxide under the action of a catalyst to form carbonate. The reaction is exothermic and volume-reducing, and low temperature and high pressure are favorable for the reaction to proceed. The reaction system mainly includes a homogeneous catalytic system and a heterogeneous catalytic system. The selection of catalyst is also the key to the smooth progress of the reaction.

Now the energy crisis is aggravating, thereby the rational use of carbon dioxide is conducive to the sustainable development of energy conservation. Carbon dioxide is used as a raw material in carbonate synthesis, which has good practical significance. There are two systems for preparing carbonate by reacting alkylene oxide with carbon dioxide, namely the homogeneous system and the heterogeneous system. A homogeneous system has problems such as the separation of products being difficult and a large amount of the catalyst being used, thereby its development is limited to a certain extent. The heterogeneous method is of relatively good industrial value, because it is in favor of the separation of the reaction product and the catalyst, and the catalyst is easily regenerated and can be recycled many times.

CN106588862A discloses a purification process and purification system of ethylene carbonate, which respectively adopt a continuous rectification column and a batch rectification column.

First, the crude product is passed into the continuous rectification column, the light components are removed at the top, the heavy components are removed at the bottom, the purified product is extracted from the side-line and passed into the batch rectification column, the light components are removed at the top, and ethylene carbonate product is extracted from the side-line. In the production run of the technology process, ethylene carbonate in the removed light component is not recovered, and the product yield is low.

CN102675276A discloses an automatically-controlled stable and continuous production process for ethylene carbonate. Its control center collects data including flow speed, flow rate, concentration, pressure, temperature, and the like measured by the sensor through the data feedback circuit and then integrates and transmits the data to the effector through the instruction output circuit to control the on-off, flow speed and flow rate of a high-pressure metering pump and achieve the purpose of balanced and continuous production. However, the production process uses a homogeneous catalyst, which has great limitations.

When carbonate is prepared by the existing gas-liquid reactor, there are still problems of insufficient reaction of raw materials and low conversion efficiency. In addition, since carbon dioxide needs to be introduced into the reactor as a reactant, the introduction of carbon dioxide can in turn lead to gas binding of the pump. Furthermore, due to the introduction of gas in the gas-liquid reaction, the liquid level fluctuates greatly, and it is difficult to accurately determine the actual liquid level of the reactor by using a traditional liquid level gauge, which can easily lead to a "full-tank" state, thus having a negative influence on the reaction operation. All of these will affect the conversion rate of the reactants, and then affect the yield, the purity, and the like of the final synthesized carbonate.

SUMMARY OF THE INVENTION

The inventors of the present invention have conducted in-depth research and found that the above-mentioned technical problems in the prior art can be solved by using the gas-liquid bubbling bed reactor of the present invention, and further, the above-mentioned technical problems in the prior art can be solved by using the reaction system of the present invention.

Furthermore, the inventors of the present invention have also found a process for producing carbonate.

Specifically, the present invention provides the following technical solutions.

According to one aspect of the present invention, there is provided a gas-liquid bubbling bed reactor, comprising a liquid distributor, a gas distributor located below the liquid distributor, a catalyst bed layer and a catalyst support plate, and an optional interception screen, wherein the top of the reactor is provided with a gas outlet, the reactor is provided with a feed inlet connected to the liquid distributor, a gas inlet connected to the gas distributor, the bottom is provided with a discharge outlet, preferably the catalyst bed is loaded with a heterogeneous catalyst.

According to one aspect of the present invention, there is provided a reaction system, which comprises the gas-liquid bubbling bed reactor of the present invention and a sub-reactor, the feed inlet of the sub-reactor is connected to the discharge outlet of the gas-liquid bubbling bed reactor, preferably the sub-reactor is a fixed bed reactor, preferably the gaseous space of the gas-liquid bubbling bed reactor is communicated with the gaseous space of the sub-reactor.

According to one aspect of the present invention, there is provided a process for synthesizing carbonate, which uses the above-mentioned gas-liquid bubbling bed reactor of the present invention, and comprises the steps: mixing alkylene oxide and a first carbon dioxide gas with a recycle stream from the reactor and sending the resulting mixture into a liquid distributor of the reactor via the feed inlet; sending a second carbon dioxide gas into a gas distributor of the reactor via a gas inlet; mixing the upward-moving second carbon dioxide gas with a downward-moving stream to react in the presence of a catalyst and obtain a carbonate-containing liquid stream, preferably the catalyst is heterogeneous.

According to one aspect of the present invention, there is provided a process for synthesizing carbonate, which uses the above-mentioned reaction system of the present invention, and comprises the steps: the carbonate-containing liquid stream is cooled by a cooler and then divided into a first stream and a second stream; the first stream as recycle stream is allowed to enter the feed inlet of the gas-liquid bubbling bed reactor successively through a circulating pump, a mixer and a dissolver; alkylene oxide is introduced into the mixer to mix with the recycle stream; a first carbon dioxide gas is introduced into the dissolver to mix with the recycle stream; a second carbon dioxide gas is allowed to enter a gas distributor of the gas-liquid bubbling bed reactor; the upward-moving second carbon dioxide gas and a downward-moving liquid phase stream are mixed and reacted in the presence of a catalyst to obtain a carbonate-containing liquid stream, preferably the catalyst is a heterogeneous catalyst; the second stream is allowed to enter the sub-reactor to continue the reaction and produce carbonate.

Invention Effect

With the gas-liquid bubbling bed reactor of the present invention and the process for synthesizing carbonate by using the gas-liquid bubbling bed reactor, carbon dioxide gas can be sufficiently dissolved in the recycle stream, thereby reducing or avoiding the dissolution time of carbon dioxide in the reactor, capable of improving the conversion efficiency of carbon dioxide and alkylene oxide, shortening the reaction time and improving the yield of carbonate, so that carbonate can be prepared efficiently in a high yield, and the carbonate product can be obtained with high purity. In addition, the gas-liquid bubbling bed reactor of the present invention can also avoid the gas binding caused by the carbon dioxide gas to the circulating pump.

Through the reaction system of the present invention and the synthesis process for synthesizing carbonate by using the reaction system, while having the above-mentioned excellent effects of the gas-liquid reactor of the present invention, the gas binding caused by carbon dioxide to the circulating pump can be effectively prevented, and the impact on productivity caused by overflow in the bubbling bed reactor can be suppressed, and the yield of carbonate can be increased. In addition, the reaction system of the present invention can solve the problem of back mixing in the reaction process in the gas-liquid bubbling bed, so that the alkylene oxide material can be sufficiently converted, and the yield of carbonate can be increased.

In addition, with the reaction system of the present invention and the synthetic process for synthesizing carbonate by using the reaction system, the crude carbonate product can be continuously rectified through two columns (a light-removing column and a heavy-removing column), most of the electronic-grade products are obtained from the top and the side-line of the heavy-removing column, and the light component and the heavy component are further purified by a batch column, thereby not only improving the yield of carbonate but also being capable of improving the purities of various grades of carbonates.

Figures 1, 2:
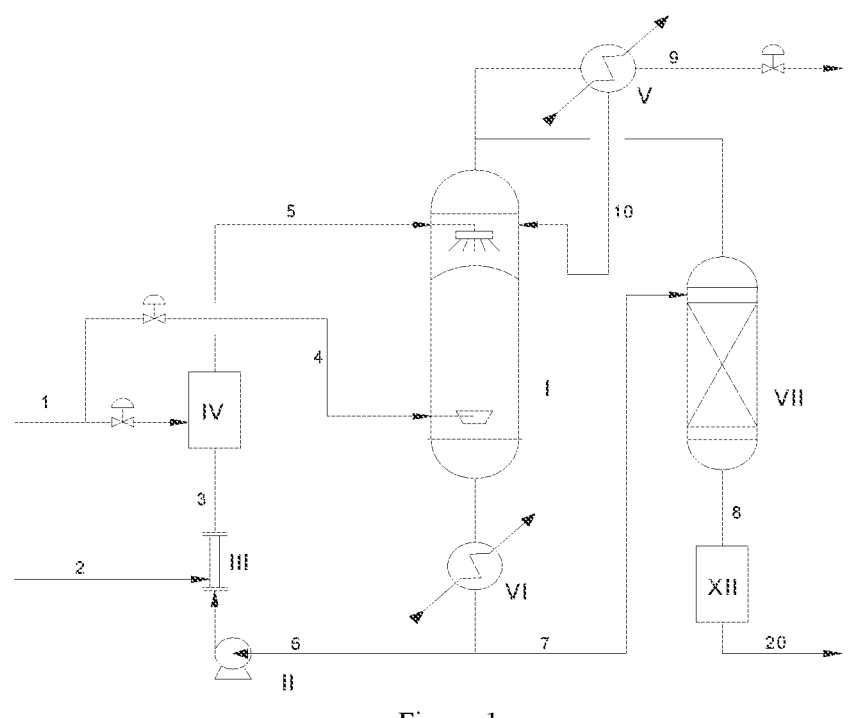
FIG. 1 is a schematic diagram of the system for synthesizing carbonate of the present invention.
FIG. 2 is a schematic diagram of the separation unit for synthesizing carbonate of the present invention.

In said figures,

| | |
|---|---|
| I | Bubbling bed reactor, |
| II | Circulating pump, |
| III | Mixer, |
| IV | Dissolver, |
| V | Condenser, |
| VI | Cooler, |
| VII | Sub-reactor, |
| XII | Separation unit, |
| VIII | Flash device, |
| IX | Light-removing column, |
| X | Heavy-removing column, |
| XI | Batch column; |
| 1 | Carbon dioxide; |
| 2 | Alkylene oxide; |
| 3 | Recycled stream; |
| 4 | Carbon dioxide; |
| 5 | Recycled stream; |
| 6 | Recycled stream; |
| 7 | Second stream; |
| 8, 20 | Crude products; |
| 9 | Carbon dioxide gas containing a trace amount of alkylene oxide; |
| 10 | Condensate; |
| 11 | Bottom liquid of the flash device; |
| 12 | Light component of the light-removing column; |
| 13 | Bottom liquid of light-removing column; |
| 14 | Light component of the heavy-removing column; |
| 15 | A mixture of carbonate and a heavy component; |
| 16 | Electronic-grade carbonate; |
| 17 | Light component or high-grade carbonate or electronic-grade carbonate of the batch column; |
| 18 | Heavy component; |
| 19 | Flash gas. |

DETAILED DESCRIPTION OF THE INVENTION

Reference will now be made in detail to the present embodiments of the present invention, but it should be understood that the scope of the invention is not limited by the embodiments, but is defined by the appended claims.

When the specification derives a material, a substance, a process, a step, a device, an element, and the like with the expression such as "known to those skilled in the art", "prior art", or a synonym thereof, it is intended that the objects derived by such a prefix encompasses those having been conventionally used in the art at the time of filing this application, but also includes those which may not be so commonly used at present, but will become known in the art as being suitable for a similar purpose.

In the context of this specification, except for what is explicitly stated, any item or matter not mentioned is directly applicable to those known in the art without any changes. Moreover, any of the embodiments described herein can be freely combined with one or more other embodiments described herein, and the resulting technical solutions or technical ideas are regarded as part of the original disclosure or the original record of the present invention, and should not be regarded as new content that has not been disclosed or anticipated in this specification unless those skilled in the art believe that the combination is unreasonable.

The present invention provides a gas-liquid bubbling bed reactor, comprising a liquid distributor, a gas distributor located below the liquid distributor, a catalyst bed layer and a catalyst support plate, and an optional interception screen, wherein the top of the reactor is provided with a gas outlet, the reactor is provided with a feed inlet connected to the liquid distributor, a gas inlet connected to the gas distributor, the bottom is provided with a discharge outlet, preferably the catalyst bed is loaded with a heterogeneous catalyst.

In the present invention, the gas-liquid reaction is not limited to the case that the starting materials need to be of gas-phase and liquid-phase but means that the reaction is carried out in a gas-liquid manner, for example, it may a reaction in which one of the reactants is of gas phase and the other of the reactants is present in the liquid phase. The gas-liquid reactor of the invention is preferably used for the preparation of carbonates, particularly preferably for the preparation of carbonates by the addition method of alkylene oxide and carbon dioxide in the presence of a heterogeneous catalyst.

In the gas-liquid bubbling bed reactor of the present invention, a catalyst bed layer is arranged, and the contact of three phases, namely, the gas phase, the liquid phase, and the solid phase as the catalyst at the catalyst bed can be strengthened through the bubbling-type reaction. The reaction is performed so that the internal temperature of the catalyst bed layer is uniform, and the conversion of alkylene oxide can be improved.

More specifically, according to the gas-liquid bubbling bed reactor of the present invention, the top is provided with a gas outlet, the reactor is provided with a feed inlet and a gas inlet, and the reactor bottom is provided with a discharge outlet, wherein the gas inlet is located relatively below the feed inlet.

Among others, the gas outlet at the top of the reactor is used for the discharge of the gaseous substance in the reaction stream. Here, the top of the reactor does not mean that the gas outlet must be located on the top wall of the reactor, and it can also mean a position on the sidewall close to the upper part of the reactor (as long as it is above the reaction liquid level), for example, a position on the sidewall of the reactor as close to the top of the reactor as possible. The feed inlet is used for feeding a liquid stream (e.g., a reaction material and reaction recycle streams). It can be arranged on the sidewall of the reactor or the top of the reactor, preferably on the sidewall of the reactor.

The gas inlet is used for feeding a gaseous stream (e.g., carbon dioxide). By arranging the gas inlet below the feed inlet, after the gaseous stream enters the reactor, the sufficient mixing of the gas-liquid streams can be achieved. It can be arranged on the sidewall of the reactor or can also be arranged on the bottom of the reactor, preferably arranged on the sidewall of the reactor and located at a position below the feed inlet.

A discharge outlet at the bottom of the reactor is used to discharge the reaction product stream and the recycle stream. Here, the bottom of the reactor does not mean that the discharge outlet must be located on the bottom wall of the reactor, and it can also mean a position on the sidewall close to the lower part of the reactor (as long as it is below the reaction liquid level), for example, a position on the sidewall of the reactor as close to the bottom of the reactor as possible.

In the gas-liquid bubbling bed reactor of the present invention, there is arranged a liquid distributor connected to the feed inlet and a gas distributor connected to the gas inlet. The gas distributor is located below the liquid distributor. The purpose of arranging both the gas distributor and the liquid distributor is for achieving a sufficient contact between the gaseous stream and the liquid stream.

In one embodiment of the present invention, the liquid distributor is located in the upper part of the reactor, and during the reaction, it can be exposed above the liquid level of the reaction, and can also be submerged below the liquid level of the reaction.

In one embodiment of the present invention, the gas distributor is located in the middle or lower part of the reactor, and when the reaction is carried out, the gas distributor is submerged below the liquid level of the reaction.

In the gas-liquid bubbling bed reactor of the present invention, there is also arranged a catalyst bed layer, and the catalyst bed layer is used to support a heterogeneous catalyst for the reaction.

In the reaction of alkylene oxide and carbon dioxide, a homogeneous catalyst or a heterogeneous catalyst can be used. Preference is given to using a heterogeneous catalyst.

In one embodiment of the present invention, in the reactor, a catalyst support plate is arranged for supporting the catalyst bed layer. The catalyst support plate can also effectively prevent carbon dioxide from entering the circulating pump and avoid the gas binding of the circulating pump.

The catalyst support plate is preferably made of stainless steel, can be in the shape of a grid or a wire mesh, and can be arranged in a plane or a non-plane.

In an embodiment of the present invention, an interception screen may also be arranged in the reactor, and the interception screen is arranged on the upper part of the reactor, higher than the catalyst bed, to prevent the solid catalyst entrained during the gas release from blocking the pipeline.

In an embodiment of the present invention, the reactor is further provided with a liquid inlet, and the liquid inlet is used for refluxing the reactant stream obtained by condensing the gaseous substance discharged from the gas outlet. The liquid inlet can be located at the top of the reactor or on the sidewall of the reactor. It is preferably located on the sidewall of the reactor.

In one embodiment of the present invention, the gas distributor is preferably tubular. By using the tubular distributor, the passages for the gas rising and the liquid falling are guaranteed, and the pressure drop of the bed is reduced.

In one embodiment of the present invention, a stirring device may be provided in the gas-liquid bubbling bed reactor. Within a range not impairing the effects of the present invention, the stirring device may be any stirring device known in the art.

In one embodiment of the present invention, the gas-liquid bubbling bed reactor further comprises: a circulating pump, which is located between the discharge outlet and the feed inlet of the reactor; a mixer, which is located between the circulating pump and the feed inlet of the reactor and is provided with a reactant inlet; a dissolver, which is located between the mixer and the feed inlet of the reactor and is provided with a reaction gas inlet, and the circulating pump, the mixer, and the dissolver are successively connected by pipelines.

According to one embodiment of the present invention, the gas-liquid bubbling bed reactor further comprises a cooler, which is located on the pipeline of the recycle stream from the discharge outlet to the feed inlet of the reactor. The cooler is used for cooling down the reaction system in the reactor. Preferably, the cooler is located on the pipeline between the discharge outlet of the reactor and the circulating pump.

In one embodiment of the present invention, the circulating pump is provided with a feed inlet and a discharge outlet; the feed inlet is connected to the discharge outlet of the reactor, and the discharge outlet is connected to the feed inlet of the mixer. In one embodiment of the present invention, when the cooler is located between the discharge outlet of the reactor and the circulating pump, the cooler is provided with a feed inlet and a discharge outlet, and the feed inlet is connected to the discharge outlet of the reactor, and the discharge outlet is connected to the feed inlet of the circulating pump.

In one embodiment of the present invention, the mixer is provided with a feed inlet, a discharge outlet, and a reactant inlet; the feed inlet is connected to the discharge outlet of the circulating pump, the discharge outlet is connected to the feed inlet of the dissolver, and the reactant inlet is used for receiving reactant raw materials.

In one embodiment of the present invention, the dissolver is provided with a feed inlet, a discharge outlet, and a reaction gas inlet; the feed inlet is connected to the discharge outlet of the mixer, the discharge outlet is connected to the feed inlet of the reactor, and the reaction gas inlet is used for receiving the reaction gas.

In one embodiment of the present invention, the chemical engineering filling manner known in the art can be used in the dissolver and the mixer to increase the disturbing mixing.

In the present invention, a dissolver is provided downstream of the circulating pump. The gas binding of the circulating pump caused by the gas can be avoided, and the problem of unstable operation caused by the gas binding during the reaction process can be avoided. Furthermore, the gas binding of the circulating pump can be further avoided by arranging the cooler before the circulating pump.

When the gas-liquid bubbling bed reactor of the present invention is used for the synthesis of carbonate from carbon dioxide and alkylene oxide, the alkylene oxide is introduced at the inlet of the mixer; a part of carbon dioxide is introduced at the inlet of the dissolver.

When synthesizing carbonate from carbon dioxide and alkylene oxide, the reaction between carbon dioxide and alkylene oxide is a dissolution reaction, and the dissolution process is the control step of the entire reaction. If a bubbling reactor is simply used, the reaction time is relatively long. In addition, carbon dioxide is soluble in both carbonate and alkylene oxide, and the solubility in carbonate can reach a concentration of 10-20% by mass. In addition, when utilizing the gas-liquid bubbling bed reactor of the present invention to carry out the preparation of carbonate, with the dissolver, before carbon dioxide enters the reactor, a part of the carbon dioxide gas is sufficiently dissolved in the recycle stream, so that the carbon dioxide content in the recycle stream is increased, thereby reducing or avoiding the dissolution time of carbon dioxide in the reactor, and improving the reaction conversion rate, so that the reaction conversion rate can reach 99% or higher. In addition, in the present invention, a dissolver is provided downstream of the mixer. The dissolution of carbon dioxide in the solute (alkylene oxide) can be increased, and the concentration of carbon dioxide in the recycle stream entering the reactor can be increased, thereby the reaction conversion can be further increased.

According to one embodiment of the present invention, the gas-liquid bubbling bed reactor further comprises a condenser, which is connected to the gas outlet of the reactor. The condenser is used for condensing the gaseous substance from the reactor and refluxing the liquid substance obtained by condensing via the liquid inlet of the reactor into the bubbling bed reactor.

In one embodiment of the present invention, the condenser is provided with a gas inlet, a gas outlet and a liquid outlet; the gas inlet is connected to the gas outlet of the reactor, and the liquid outlet is connected to the liquid inlet of the reactor.

According to another aspect of the present invention, there is provided a process for synthesizing carbonate, which uses the above-mentioned gas-liquid bubbling bed reactor of the present invention, and comprises the steps:

mixing alkylene oxide and a first carbon dioxide gas with a recycle stream from the reactor and sending the resulting mixture into a liquid distributor of the reactor via the feed inlet;

sending a second carbon dioxide gas into a gas distributor of the reactor via a gas inlet; and mixing the upward-moving second carbon dioxide gas with a downward-moving stream to react in the presence of a catalyst and obtain a carbonate-containing liquid stream.

In one embodiment of the present invention, the recycle stream flowing out of a discharge outlet of the reactor flows through a cooler and a circulating pump, then mixes in a mixer with alkylene oxide introduced from an inlet of the mixer, and then mixes in a dissolver with the first carbon dioxide introduced from an inlet of the dissolver, and then enters the liquid distributor of the reactor via a feed inlet.

In one embodiment of the present invention, a gas substance from the reactor is allowed to enter a condenser to carry out the gas-liquid separation, and the obtained liquid is returned to the gas-liquid bubbling bed reactor via a liquid inlet.

In one embodiment of the present invention, based on the total mass of carbon dioxide introduced into the reactor, the partition ratio of the first carbon dioxide gas to the second carbon dioxide gas is (1-50):(50-99), preferably (10-50):(50-90).

In one embodiment of the present invention, in the initial preparation of carbonate, a solvent may or may not be used. Various carbonates can be used as the solvent, preferably the solvent is the same as the carbonate to be prepared. After the preparation is started, since the prepared carbonate itself can be used as the reaction solvent, during the preparation process, a fresh solvent may be further added separately, or the prepared carbonate may be directly used as the reaction solvent without the addition of the fresh solvent.

In the present invention, the recycle stream refers to a stream from the bubbling bed reactor, which contains the reaction solvent, the reaction raw materials, the reaction intermediate, the reaction product (which may be the reaction solvent), and the like. In the present invention, when the reactant stream is circulated outside the main reactor, the composition of the recycle stream changes due to the change in temperature and the introduction of alkylene oxide and carbon dioxide as reactants. The composition of the recycle stream is not intended to be limited in the present invention.

In the present invention, as the alkylene oxide, ethylene oxide, 1,2-propylene oxide, 1,3-propylene oxide, butylene oxide and the like can be used, but the alkylene oxide is not limited thereto.

In one embodiment of the present invention, in the above-mentioned process for synthesizing carbonate, the catalyst used in the bubbling bed reactor is heterogeneous, and the ratio of the density of the catalyst to the density of the reactant (a liquid mixture of alkylene oxide and carbonate) is 0.3-2, preferably 0.5-1.5. As the kind of catalyst, those conventionally used in the art, such as resin-based catalysts, can be used.

The density of the catalyst is close to the density of the reactants, and the catalyst is in a suspended state during the gas-liquid mixing and the reaction, which is beneficial to the distribution of the gas in the reactor; if the density of the catalyst is too high, the gas distributor will be wrapped by the catalyst, and the effect of the catalytic reaction is poor.

In the reaction of synthesizing carbonate from alkylene oxide and carbon dioxide, the most commonly used catalyst in the industry is a homogeneous catalyst. Therefore, there are catalysts both in the recycle stream and in the reaction product. Therefore, after the reaction, it is necessary to separate and recycle the catalyst, which increases the complexity of the process and the difficulty of operation. The present invention adopts a heterogeneous catalyst and directly separates the catalyst from the reactant and the reaction product in the reactor, thereby avoiding the increase in the additional equipment and the energy consumption due to the subsequent separation of the catalyst. Moreover, in the reactor of the present invention, the arrangement of the catalyst bed layer can strengthen the contact of three phases, namely, the gas phase, the liquid phase, and the solid phase as the catalyst at the catalyst bed. The reaction is performed so that the internal temperature of the catalyst bed layer is uniform, and the conversion of alkylene oxide can be improved.

In one embodiment of the present invention, the bubbling bed reactor is subjected to a heat quantity regulation and control with a cooler through external circulation heat removal, and the temperature of the catalyst bed layer is controlled by the circulation amount of the circulating pump. On a mass basis, the recycled amount is 10-100 times the alkylene oxide feed amount.

The gas from the reactor top will entrain a small amount of alkylene oxide and carbonate. Carbonate is easy to crystallize and precipitate at a temperature below 40° C., causing the blockage of pipelines and/or valves. Therefore, in the present invention, the gas from the top of the bubbling bed reactor is condensed by the condenser and then discharged out from a gas absorption device via a gas pressure controller, and the condensation temperature is not lower than 40° C.

In one embodiment of the present invention, the molar ratio of alkylene oxide to carbon dioxide in the reaction is in the range commonly used in the art, for example, the molar ratio of carbon dioxide to alkylene oxide can be 1:1-10:1, preferably 1:1-2:1.

In one embodiment of the present invention, the temperature, the pressure, and the like for the reaction of alkylene oxide and carbon dioxide can be those conventional in the art. For example, the reaction pressure can be 1-10 MPa (gauge pressure), and the reaction temperature can be 80-300° C.

In another aspect of the present invention, there is provided a reaction system, which comprises the above-mentioned gas-liquid bubbling bed reactor of the present invention (sometimes also referred to as the main reactor in the present invention) and a sub-reactor, the feed inlet of the sub-reactor is connected to the discharge outlet of the gas-liquid bubbling bed reactor.

In one embodiment of the present invention, the sub-reactor may be a reactor conventionally chosen in the art, as long as the reaction of the reactants (e.g., carbon dioxide and alkylene oxide) in the reaction stream can be completed. The sub-reactor may not have a reactant gas inlet since it is possible not to introduce the gas reactant into the sub-reactor. In one embodiment of the present invention, the sub-reactor is preferably a fixed bed reactor.

In one embodiment of the present invention, it is unnecessary to introduce a fresh (additional) reaction raw material to the sub-reactor.

In one embodiment of the present invention, the feed inlet of the sub-reactor is connected to a position between the discharge outlet of the main reactor and the circulating pump via a connection pipeline. In one embodiment of the present invention, in case the main reactor has a cooler, the feed inlet of the sub-reactor is connected to a position between the cooler of the main reactor and the circulating pump via a connection pipeline.

In one embodiment of the present invention, the top of the sub-reactor is provided with a gas outlet, the bottom of the sub-reactor is provided with a discharge outlet, and the feed inlet is connected to the discharge outlet of the main reactor. Here, the gas outlet at the top of the sub-reactor does not mean that the gas outlet must be located on the top wall of the sub-reactor, and it can also mean a position on the sidewall close to the upper part of the sub-reactor (as long as it is above the reaction liquid level), for example, a position on the sidewall of the sub-reactor as close to the top of the sub-reactor as possible. The discharge outlet at the bottom of the sub-reactor does not mean that the discharge outlet must be located on the bottom wall of the sub-reactor, and it can also mean a position on the sidewall close to the lower part of the sub-reactor (as long as it is below the reaction liquid level), for example, a position on the sidewall of the sub-reactor as close to the bottom of the sub-reactor as possible. The feed inlet of the sub-reactor can be arranged on the sidewall of the reactor or the top of the reactor, preferably on the sidewall of the reactor.

Due to the countercurrent contact of the gas and the liquid in the main reactor, there is a back mixing in the reaction process, resulting in the streams (such as the stream containing alkylene oxide) cannot be completely converted. Therefore, the present invention does not need to introduce fresh (additional) reaction raw materials (such as carbon dioxide, alkylene oxide) into the sub-reactor, but allows the saturatedly dissolved reactants (such as carbon dioxide, alkylene oxide) in the reaction product from the main reactor to continue to react in the sub-reactor in a manner similar to plug flow. Thereby, the conversion rate of the reactant can be further improved.

On the other hand, in the case of using the reaction system of the present invention to synthesize carbonate from carbon dioxide and alkylene oxide, after carbon dioxide is passed into the reactor, due to the influence of the density difference, the liquid level fluctuates greatly. It is difficult to use a traditional liquid level gauge to accurately determine the actual liquid level of the reactor, which can easily lead to a "full tank" state. Therefore, in the preferred embodiment of the present invention, the discharge outlet of the main reactor is connected to the feed inlet of the sub-reactor through the pipeline, so that the main reactor and the sub-reactor are connected in series, and the gas-phase spaces of the two reactors are communicated, and the liquid of the main reactor enters the sub-reactor in an overflowing manner. At this time, the position of the feed inlet of the sub-reactor is not below the filling height of the catalyst bed layer of the main reactor, and not above the height of the liquid distributor of the main reactor.

In one embodiment of the present invention, the main reactor and the sub-reactor are connected in series, the gas phase spaces are communicated, and the liquid of the main reactor enters the sub-reactor in an overflowing manner. In one embodiment of the present invention, the position of the feed inlet of the sub-reactor is not below the filling height of the catalyst bed layer of the main reactor, and not above the height of the liquid distributor of the main reactor.

In one embodiment of the present invention, the gas outlet of the sub-reactor is connected to the above-mentioned condenser. More specifically, the condenser is used for condensing the gaseous substance from the sub-reactor and refluxing the condensed liquid substance into the main reactor through the liquid inlet of the main reactor.

In one embodiment of the present invention, the gas inlet of the condenser is connected to the gas outlet of the sub-reactor. The gas from the sub-reactor top will entrain a small amount of alkylene oxide and carbonate. Carbonate is easy to crystallize and precipitate at a temperature below 40° C., causing the blockage of pipelines and valves. In the present invention, the gas from the top of the sub-reactor is condensed by the condenser and then discharged out from a gas absorption device via a gas pressure controller, and the condensation temperature is not less than 40° C.

According to one embodiment of the present invention, the reaction system further comprises a separation unit, which is connected to the discharge outlet of the sub-reactor.

In one embodiment of the present invention, the separation unit includes:

a flash device, the feed inlet of which is connected to the discharge outlet of the sub-reactor;

a light-removing column, the feed inlet of which is connected to the discharge outlet of the flash device;

a heavy-removing column, the feed inlet of which is connected to the discharge outlet of the light-removing column;

a batch column, the feed inlet of which is connected to the liquid outlets of the light-removing column and the heavy-removing column.

In one embodiment of the present invention, the flash device can adopt conventional flash devices in the art, which are preferably selected from a flash drum, a flash column, and a film evaporator, and are continuously operated at atmospheric pressure or negative pressure. The flash device is preferably provided with heating by coil pipe or jacket, and the heating temperature is 110-160° C.

In one embodiment of the present invention, the light-removing column, the heavy-removing column, and the batch column can all adopt light-removing columns, heavy-removing columns, and batch columns conventional in the art.

In one embodiment of the present invention, the light-removing column can adopt conventional light-removing columns in the art, its operation pressure is 0-5 KPa, the column bottom temperature is less than 160° C., preferably less than 150° C., and it is continuously operated.

In one embodiment of the present invention, the heavy-removing column can adopt conventional heavy-removing columns in the art, its operation pressure is 0-5 KPa, the column bottom temperature is less than 160° C., preferably less than 150° C., and it is continuously operated. In one embodiment of the present invention, the product can be withdrawn from the sideline of the heavy-removing column, as required.

In one embodiment of the present invention, the light components obtained from the light-removing column and the heavy-removing column, and the column bottom liquid of the heavy-removing column respectively enter the batch column for further separation, the light components are obtained from the column top, and the heavy components are obtained from the column bottom. The batch column can adopt conventional batch columns in the art, its operation pressure is 0-5 KPa, the column bottom temperature is less than 160° C., preferably less than 150° C., and it is operated in a batch manner.

The structure form and the filler selection of the above separation unit are designed on the premise that the pressure drop of the separation system is the smallest one and the temperature of the column bottom is the lowest one.

On the other hand, the present invention provides a process for synthesizing carbonate, which uses the above-mentioned reaction system of the present invention, and comprises the steps:

the carbonate-containing liquid stream is cooled by a cooler and then divided into a first stream and a second stream;

the first stream as recycle stream is allowed to enter the feed inlet of the gas-liquid bubbling bed reactor (also known as the main reactor in the present invention) successively through a circulating pump, a mixer, and a dissolver;

alkylene oxide is added into the mixer to mix with the recycle stream;

a first carbon dioxide gas is added into the dissolver to mix with the recycle stream;

a second carbon dioxide gas is allowed to enter the gas distributor of the gas-liquid bubbling bed reactor;

the upward-moving second carbon dioxide gas and a downward-moving liquid phase stream are mixed and reacted in the presence of a catalyst to obtain a carbonate-containing liquid stream, the second stream is allowed to enter the sub-reactor to continue the reaction and produce carbonate.

In one embodiment of the present invention, the process for synthesizing carbonate further comprises the steps: gas substances from the main reactor and the sub-reactor are allowed to enter a condenser to carry out the gas-liquid separation, and the obtained liquid is returned to the main reactor via a liquid inlet.

In one embodiment of the present invention, no fresh (additional) carbon dioxide and alkylene oxide as raw materials are passed through the sub-reactor. In one embodiment of the present invention, the heat removal is preferably performed with jacket and/or coil pipe, and the reaction product of the sub-reactor is a crude carbonate product that does not comprise a catalyst.

In the present invention, in case the above-mentioned reaction system of the present invention is used to carry out the process of synthesizing carbonate, based on the total mass of carbon dioxide introduced into the main reactor, the partition ratio of the first carbon dioxide gas to the second carbon dioxide gas is (1-50):(50-99), preferably (10-50):(50-90).

In the above-mentioned process for synthesizing carbonate by using the reaction system of the present invention, the recycle stream refers to a stream from the main reactor, which contains the reaction solvent, the reaction raw materials, the reaction intermediate, the reaction product (which may be the reaction solvent), and the like. In the present invention, when the reactant stream is circulated outside the main reactor, the composition of the recycle stream changes due to the change in temperature and the introduction of alkylene oxide and carbon dioxide as reactants. The composition of the recycle stream is not intended to be limited in the present invention.

In the above-mentioned process for synthesizing carbonate by using the reaction system of the present invention, ethylene oxide, 1,2-propylene oxide, 1,3-propylene oxide, butylene oxide and the like can be used as the alkylene oxide, but the alkylene oxide is not limited thereto.

In one embodiment of the present invention, in the above-mentioned process for synthesizing carbonate, the catalyst used in the main reactor is heterogeneous, and the ratio of the density of the catalyst to the density of the reactant (a liquid mixture of alkylene oxide and carbonate) is 0.3-2, preferably 0.5-1.5. As the kind of catalyst, those conventionally used in the art, such as resin-based catalysts, can be used.

The density of the catalyst is close to the density of the reactants, and the catalyst is in a suspended state during the gas-liquid mixing and the reaction, which is beneficial to the distribution of the gas in the reactor; if the density of the catalyst is too high, the gas distributor will be wrapped by the catalyst, and the effect of the catalytic reaction is poor.

In one embodiment of the present invention, the process further comprises that the crude carbonate product obtained from the sub-reactor is allowed to enter a separation unit, and comprises the steps:

the crude carbonate product is allowed to enter a flash device for treatment to obtain a liquid stream and a gas, and the gas is emitted;

the liquid stream obtained from the flash device is allowed to enter a light-removing column for treatment to obtain a column top light component and a bottom liquid;

the bottom liquid obtained from the light-removing column is allowed to enter a heavy-removing column for treatment to produce a column top light component, an electronic-grade carbonate, a high-grade carbonate, and a mixture of carbonate and heavy component, or to produce a light component, an electronic-grade carbonate, and a mixture of carbonate and heavy component;

the light components obtained from the light-removing column and the heavy-removing column and the bottom liquid obtained from the heavy-removing column are allowed to enter a batch column to produce a light component, a high-grade carbonate, an electronic-grade carbonate, and a heavy component.

In one embodiment of the present invention, the flash device can adopt conventional flash devices in the art, which are preferably selected from a flash drum, a flash column, and a film evaporator, and are continuously operated at atmospheric pressure or negative pressure. The flash device is preferably provided with heating by coil pipe or jacket, and the heating temperature is 110-160° C.

In one embodiment of the present invention, the light-removing column can adopt conventional light-removing columns in the art, its operation pressure is 0-5 KPa, the column bottom temperature is less than 160° C., preferably less than 150° C., and it is continuously operated; its column top light component includes diols and homologs thereof.

In one embodiment of the present invention, the heavy-removing column can adopt conventional heavy-removing columns in the art, its operation pressure is 0-5 KPa, the column bottom temperature is less than 160° C., preferably less than 150° C., and it is continuously operated; Its column top light component includes diols and carbonates; an electronic-grade carbonate is withdrawn from the side-line above the feeding position, a high-grade carbonate is withdrawn from the side-line below the feeding position, a heavy component is withdrawn from the column bottom, or a mixture of carbonate and heavy component is directly withdrawn from the column bottom.

In one embodiment of the present invention, the light components obtained from the light-removing column and the heavy-removing column, and the column bottom liquid of the heavy-removing column respectively enter the batch column for further separation, the light components, the high-grade carbonate, and the electronic-grade carbonate are obtained from the column top, and the heavy components are obtained from the column bottom. The batch column can adopt conventional batch columns in the art, its operation pressure is 0-5 KPa, the column bottom temperature is less than 160° C., preferably less than 150° C., and it is operated in a batch manner.

The structure form and the filler selection of the above separation unit are designed on the premise that the pressure drop of the separation system is the smallest one and the temperature of the column bottom is the lowest one.

More specifically, the process flow of the system for synthesizing carbonate of the present invention is described as follows:

the raw material alkylene oxide is metered in terms of the flow rate and mixed with the recycle stream of the main reactor followed by entering the liquid distributor of the main reactor; a part of raw material carbon dioxide is controlled in terms of the flow rate and dissolved in the recycle stream of the main reactor, another part is controlled in terms of the flow rate and sent to the gas distributor of the main reactor, the reaction heat of the main reactor is removed by means of the external circulation cooling, the reaction product is sent to the sub-reactor in an overflow manner to continue the reaction, wherein the gas phase spaces of the main reactor and the sub-reactor are communicated, the gas-phase product is condensed by the condenser and discharged via the gas phase pressure control, and the condensate is refluxed to the main reactor; the reaction product of the sub-reactor is sent to a subsequent separation system, wherein the reaction product is firstly passed through a flash tank, the resulting non-condensable gas is sent to be processed, and the resulting liquid phase is sent to a light-removing column, by which a heavy component is obtained, and the heavy component is sent to a heavy-removing column from the bottom or the side-line of the light-removing column for the further separation; a mixture of the high-grade carbonate and the heavy component is obtained from the bottom of the heavy-removing column, or the high-grade carbonate is obtained below the feeding position of the heavy-removing column, a mixture of carbonate and the heavy component is obtained from the column bottom, an electronic-grade carbonate product useful for the power lithium battery is obtained from the side-line; the light components obtained from the light-removing column and the heavy-removing column and the column bottom liquid obtained from the heavy-removing column are sent to the batch column for a further treatment, the column top non-condensable gas is sent to be processed, and the products such as high-grade carbonate and electronic-grade carbonate can be further obtained from the column top or by liquid cutting from the side-line.

According to the process of the present invention, the yield of the obtained electronic-grade carbonate product is not less than 70%, more preferably not less than 85%. With the process of the present invention, the problems of the low conversion rate, the gas binding of the circulating pump, the unstable operation, the low yield of electronic-grade products, and the like in the carbonate synthesis process are solved purposedly, and the present invention can be applied to related industrial production.

EXAMPLES

The present invention will be further described below through examples, but the present invention is not limited to these examples.

Example 1

100 kg/h ethylene oxide was metered in terms of flow rate, mixed with a recycle stream of the main reactor, and then sent to the main reactor; the raw material carbon dioxide was controlled in terms of the flow rate, 5 kg/h of which was dissolved in the recycle stream of the main reactor and 115 kg/h of which was sent to the gas distributor of the main reactor, the gas distributor adopted a tubular distributor; the pressure of the main reactor was 1.5 MPa, the temperature was 100° C., the circulating rate was 3000 kg/h, the temperature rise of the reactor was 40° C., the reaction product was sent to the sub-reactor in an overflow manner to continue the reaction, the operation conditions of the sub-reactor were identical to those of the main reactor, the temperature rise was less than 10° C., the gas-phase spaces of the main reactor and the sub-reactor were communicated, the gas-phase product was condensed to 45° C. by an external condenser and discharged via the gas phase pressure control, and the condensate was refluxed to the main reactor. The EO conversion rate of the main reactor was ≥85%.

The reaction product of the sub-reactor contained 99% of ethylene carbonate, 0.5% of ethylene glycol, 0.3% of diethylene glycol, and 0.2% of other homologs. The product was sent to a subsequent separation system. Firstly, the product was sent to a flash column. The flash column adopted a filler, the filler type was BX500, and the filler height was 3 m. The flash column was operated at normal pressure and heated by steam. The column bottom temperature was controlled to 160° C. After the flash separation, the resulting non-condensable gas was sent to be processed, and the resulting liquid phase was sent to a light-removing column. The operation pressure for the light-removing column was 5 kPa, and the column bottom temperature was controlled to 160° C. The column bottom liquid of the light-removing column was sent to the heavy-removing column for further separation. The operation pressure for the heavy-removing column was 5 kPa, and the column bottom temperature was controlled to 160° C. A high-grade ethylene carbonate was obtained from the column bottom of the heavy-removing column. An electronic-grade ethylene carbonate product useful for the power lithium battery was cut from the side-line alone. The light components obtained from the light-removing column and the heavy-removing column and the column bottom liquid obtained from the heavy-removing column were sent to a batch column for further treatment. The operation pressure for the batch column was 5 kPa, and the column bottom temperature was controlled to 160° C. The column top non-condensable gas was sent to be processed, and the products such as high-grade ethylene carbonate and electronic-grade ethylene carbonate could be further obtained from the column top or the side-line liquid. The filler types for the light-removing column, the heavy-removing column, and the batch column were BX500, and the filler heights were 12 m.

By the above separation, the electronic-grade product had a yield of ≥70%, purity of ≥99.99%, and chromaticity of ≤10; and the high-grade product had a yield of ≥25%, purity of ≥99.95%, and chromaticity of ≤20.

Example 2

This example was identical to Example 1, except that the raw material carbon dioxide was controlled in terms of the flow rate, 20 kg/h of which was dissolved in the recycle stream of the main reactor and 115 kg/h of which was sent to the gas distributor of the main reactor. The temperature rise of the sub-reactor is ≤6° C. The EO conversion rate of the main reactor was ≥87%, and the content of ethylene carbonate in the reaction product of the sub-reactor was ≥95%.

By the separation process, the electronic-grade product had a yield of ≥70%, purity of ≥99.99%, and chromaticity of ≤10; and the high-grade product had a yield of ≥25%, purity of ≥99.95%, and chromaticity of ≤20.

Example 3

This example was identical to Example 1, except that the pressure of the main reactor was 2.0 MPa, the temperature was 80° C., the circulating rate was 4000 kg/h, and the temperature rise of the reactor was 25° C. The EO conversion rate of the main reactor was ≥90%, and the content of ethylene carbonate in the reaction product of the sub-reactor was ≥95%.

By the separation process, the electronic-grade product had a yield of ≥70%, purity of ≥99.99%, and chromaticity of ≤10; and the high-grade product had a yield of ≥25%, purity of ≥99.95%, and chromaticity of ≤20.

Example 4

This example was identical to Example 1, except that the operating pressure of the batch column was 1 kPa, the column bottom temperature was ≤155° C., the filler type was CY900, the filler height was 12 m, the column top light component was discharged and collected, the side-line or/and the column bottom were returned to the light-removing column.

By the separation process, the electronic-grade product had a yield of ≥70%, purity of ≥99.99%, and chromaticity of ≤10; and the high-grade product had a yield of ≥28%, purity of ≥99.95%, and chromaticity of ≤20.

Example 5

This example was identical to Example 1, except that the flash device was a flash drum, the operation pressure was 10 kPa, the temperature was controlled to 120° C.; the light-removing column and the batch column: the operation pressure 3 kPa, the column bottom temperatures ≤155° C., the filler types CY700, the filler heights 15 m; the condensers of the above-mentioned rectifying columns were all internally placed at the column tops of the rectifying columns, the column bottoms adopted film evaporators, and the circularity was enforced.

By the above separation, the electronic-grade product had a yield of ≥75%, purity of ≥99.99%, and chromaticity of ≤10; and the high-grade product had a yield of ≥23%, purity of ≥99.95%, and chromaticity of ≤20.

Example 6

This example was identical to Example 1, except that the raw material carbon dioxide was controlled in terms of the flow rate, 15 kg/h of which was dissolved in the recycle stream of the main reactor and 100 kg/h of which was sent to the gas distributor of the main reactor. The pressure of the main reactor was 2.0 MPa, the temperature was 80° C., the circulating rate was 5000 kg/h, and the temperature rise of the reactor was 15° C. The EO conversion rate of the main reactor was ≥95% and the content of ethylene carbonate in the reaction product of the sub-reactor was ≥99.5%.

Flash column, the operation pressure: 0.5 kPa, the column bottom temperature: ≤150° C., the filler-type: BX500, and the filler height: 4 m;

Light-removing column, the operation pressure: 0.5 kPa, the column bottom temperature: ≤150° C., the filler-type: CY900, and the filler height: 18 m;

Heavy-removing column, the operation pressure: 0.5 kPa, the column bottom temperature: ≤150° C., the filler-type: CY900, and the filler height: 18 m;

Batch column, the operation pressure: 0.5 kPa, the column bottom temperature: ≤150° C., the filler-type: CY900, and the filler height: 10 m, the light component was cut out, and the concentrated ethylene carbonate was returned to the light-removing column.

The condensers of the above-mentioned rectifying columns were all internally placed at the column tops of the rectifying columns, the column bottoms adopted film evaporators, and the circularity was enforced.

By the above separation, the electronic-grade product had a yield of ≥85%, purity of ≥99.99%, and chromaticity of ≤10; and the high-grade product had a yield of ≥13%, purity of ≥99.95%, and chromaticity of ≤20.

Example 7

This example was identical to Example 1, except that the raw materials were propylene oxide and carbon dioxide, which reacted to generate propylene carbonate. The PO conversion rate of the main reactor was ≥85%, and the content of propylene carbonate in the reaction product of the sub-reactor was ≥95%.

The flash device was a flash drum, the operation pressure was 10 kPa, and the temperature was controlled to 120° C.; the light-removing column and the batch column: the operation pressure 1 kPa, the column bottom temperatures ≤160° C., the filler types CY700, the filler heights 20 m; the condensers of the above-mentioned rectifying columns were all internally placed at the column tops of the rectifying columns, the column bottoms adopted film evaporators, and the circularity was enforced.

By the above separation, the electronic-grade product had a yield of ≥70%, purity of ≥99.99%, and chromaticity of ≤10; and the high-grade product had a yield of ≥25%, purity of ≥99.5%, and chromaticity of ≤30.

Example 8

This example was identical to Example 1, except that carbon dioxide was introduced with a mixer, by which the flow rate was controlled to 84 kg/h (i.e., 70%), and with a gas distributor, by which the flow rate was controlled to 36 kg/h (i.e., 30%). The EO conversion of the main reactor decreased due to the reduced dissolution of carbon dioxide in the main reactor. The EO conversion rate of the main reactor was ≥80%, and the temperature rise of the sub-reactor was 10° C.

Comparative Example 1

This example was identical to Example 1, except that carbon dioxide was not introduced through the mixer, but all carbon dioxide was passed through the gas inlet of the reactor and introduced into the main reactor through the gas distributor, and the EO conversion rate of the main reactor was reduced by 3%. The temperature rise of the sub-reactor was 10° C.

Any reference to any numerical value in this specification includes all values in increments of one unit from the lowest value to the highest value provided that there was a gap for at least two units between any lowest value and any highest value. For example, if an amount of a component was stated, or a process variable such as temperature, pressure, time, etc. has a value of 50-90, in this specification it means that the numerical values such as 51-89, 52-88 . . . and 69-71 and 70-71 were specifically enumerated. For non-integer values, 0.1, 0.01, 0.001 or 0.0001 may be considered as one unit, as appropriate. These are just some specially specified examples. In this application, in a similar manner, all possible combinations of numerical values between the enumerated lowest and highest values were considered to have been disclosed.

It should be noted that the above-mentioned embodiments are only used to explain the present invention, and do not constitute any limitation to the present invention. The present invention has been described with reference to exemplary embodiments, but it is to be understood that the words used therein are words of description and explanation, rather than words of limitation. The present invention may be modified within the scope of the claims of the present invention as specified and may be modified without departing from the scope and spirit of the present invention. Although the present invention described herein refers to the specific methods, materials, and embodiments, it is not intended to be limited to the specific examples disclosed therein, but rather, the present invention extends to all other methods and applications having the same function.

The invention claimed is:

1. A gas-liquid bubbling bed reactor, comprising a liquid distributor, a gas distributor located below the liquid distributor, a catalyst bed layer and a catalyst support plate, and an optional interception screen, wherein the top of the reactor is provided with a gas outlet, the reactor is provided with a feed inlet connected to the liquid distributor, a gas inlet connected to the gas distributor, the bottom is provided with a discharge outlet, and the catalyst bed is loaded with a heterogeneous catalyst, and further comprising: a circulating pump, which is located between the discharge outlet and the feed inlet of the reactor; a mixer, which is located between the circulating pump and the feed inlet of the reactor, and is provided with a reactant inlet; a dissolver, which is located between the mixer and the feed inlet of the reactor, and is provided with a reaction gas inlet, and the circulating pump, the mixer, and the dissolver are successively connected by pipelines.

2. The reactor according to claim 1, wherein, the liquid distributor is located in the upper part of the reactor, the gas distributor is located in the middle or lower part of the reactor, and the interception screen is located above the catalyst bed.

3. The reactor according to claim 1, further comprising: a cooler located on the pipeline between the discharge outlet of the reactor and the circulating pump.

4. The reactor according to claim 3, further comprising: a condenser, which is connected to the gas outlet of the reactor, and a gas inlet of the condenser is connected to the gas outlet of the reactor, and a liquid outlet of the condenser is connected to a liquid inlet of the reactor.

5. A reaction system, which comprises the gas-liquid bubbling bed reactor according to claim 4 and a sub-reactor, a feed inlet of the sub-reactor is connected to the discharge outlet of the gas-liquid bubbling bed reactor, and a gaseous space of the gas-liquid bubbling bed reactor is communicated with a gaseous space of the sub-reactor.

6. The reaction system according to claim 5, wherein the top of the sub-reactor is provided with a gas outlet, the bottom is provided with a discharge outlet, and the gas outlet is connected to the condenser, the sub-reactor is not provided with a reaction gas inlet, and the feed inlet of the sub-reactor is connected to a position between the discharge outlet of the bubbling bed reactor and the circulating pump through a connection pipeline.

7. The reaction system according to claim 5, further comprising: a separation unit, which is connected to a discharge outlet of the sub-reactor.

8. The reaction system according to claim 7, wherein the separation unit comprises: a flash device, the feed inlet of which is connected to the discharge outlet of the sub-reactor; a light-removing column, the feed inlet of which is connected to a discharge outlet of the flash device; a heavy-removing column, the feed inlet of which is connected to a discharge outlet of the light-removing column; and a batch column, the feed inlet of which is connected to liquid outlets of the light-removing column and the heavy-removing column.

9. The reactor according to claim 1, wherein the gas distributor is a tubular distributor.

10. The reaction system according to claim 5, wherein the sub-reactor is a fixed bed reactor.

11. The reaction system according to claim 6, wherein the feed inlet of the sub-reactor is connected to a position between the cooler of the bubbling bed reactor and the circulating pump.

12. The reaction system according to claim 6, wherein a position of the feed inlet of the sub-reactor is not below the filling height of the catalyst bed layer of the gas-liquid bubbling bed reactor, and is not above the height of the liquid distributor of the gas-liquid bubbling bed reactor.

13. A process for synthesizing carbonate, which uses the gas-liquid bubbling bed reactor according to claim 1, and comprises:

mixing alkylene oxide and a first carbon dioxide gas with a recycle stream from the reactor, and sending the resulting mixture into a liquid distributor of the reactor via the feed inlet;

sending a second carbon dioxide gas into a gas distributor of the reactor via a gas inlet; and mixing the upward-moving second carbon dioxide gas with a downward-moving stream to react in the presence of a catalyst and obtain a carbonate-containing liquid stream, and the catalyst is a heterogeneous catalyst.

14. The process according to claim 13, wherein the recycle stream flowing out of a discharge outlet of the reactor flows through a cooler and a circulating pump, then mixes in a mixer with alkylene oxide introduced from an inlet of the mixer, and then mixes in a dissolver with the first carbon dioxide introduced from an inlet of the dissolver, and then enters the liquid distributor of the reactor via a feed inlet.

15. The process for synthesizing carbonate according to claim 13, wherein a gas substance from the reactor is allowed to enter a condenser to carry out the gas-liquid separation, and the obtained liquid is returned to the gas-liquid bubbling bed reactor via a liquid inlet.

16. The process according to claim 13, wherein based on the total mass of carbon dioxide introduced into the gas-liquid bubbling bed reactor, the partition ratio of the first carbon dioxide gas to the second carbon dioxide gas is (1-50):(50-99).

17. The process according to claim 13, wherein the ratio of the density of the catalyst to the density of the reactants (a mixture of alkylene oxide and carbonate) is 0.3-2, the molar ratio of carbon dioxide and alkylene oxide is 1:1-10:1; the reaction pressure is 1-10 MPa, and the reaction temperature is 80-300° C.

18. The process according to claim 16, wherein the partition ratio of the first carbon dioxide gas to the second carbon dioxide gas is (10-50):(50-90).

19. The process according to claim 17, wherein the ratio of the density of the catalyst to the density of the reactants (a mixture of alkylene oxide and carbonate) is 0.5-1.5, the molar ratio of carbon dioxide and alkylene oxide is 1:1-2:1.

20. A process for synthesizing carbonate, which uses the reaction system according to claim 5, and comprises:

cooling the carbonate-containing liquid stream by a cooler and then dividing the obtained carbonate-containing liquid stream into a first stream and a second stream;

wherein the first stream as recycle stream is allowed to enter the feed inlet of the gas-liquid bubbling bed reactor successively through a circulating pump, a mixer, and a dissolver;

alkylene oxide is introduced into the mixer to mix with the recycle stream;

a first carbon dioxide gas is introduced into the dissolver to mix with the recycle stream;

a second carbon dioxide gas is allowed to enter a gas distributor of the gas-liquid bubbling bed reactor;

the upward-moving second carbon dioxide gas and a downward-moving liquid phase stream are mixed and reacted in the presence of a catalyst to obtain a carbonate-containing liquid stream, and the catalyst is a heterogeneous catalyst;

the second stream is allowed to enter the sub-reactor to continue the reaction and produce carbonate.

21. The process for synthesizing carbonate according to claim 20, wherein gas substances from the gas-liquid bubbling bed reactor and the sub-reactor are allowed to enter a condenser to carry out the gas-liquid separation, and the obtained liquid is returned to the gas-liquid bubbling bed reactor via a liquid inlet.

22. The process according to claim 20, wherein the process further comprises entering the carbonate product obtained from the sub-reactor into a separation unit, wherein said entering comprises the following steps:

entering the crude carbonate product into a flash device for treatment to obtain a liquid stream and a gas;

entering the liquid stream obtained from the flash device into a light-removing column for treatment to obtain a light component and a bottom liquid;

wherein the bottom liquid obtained from the light-removing column is allowed to enter a heavy-removing column for treatment to produce a light component, an electronic-grade carbonate, a high-grade carbonate, and a mixture of carbonate and heavy component, or to produce a light component, an electronic-grade carbonate, and a mixture of carbonate and heavy component;

further wherein the light components obtained from the light-removing column and the heavy-removing column and the bottom liquid obtained from the heavy-removing column are allowed to enter a batch column to produce a light component, a high-grade carbonate, an electronic-grade carbonate, and a heavy component.

* * * * *